US00PP18191P2

(12) United States Plant Patent
Gerawan

(10) Patent No.: US PP18,191 P2
(45) Date of Patent: Nov. 13, 2007

(54) PEACH TREE NAMED 'GP10'

(50) Latin Name: *Prunus persica*
Varietal Denomination: GP10

(76) Inventor: Mike Gerawan, 21249 E. Jefferson, Reedley, CA (US) 93654

( * ) Notice: Subject to any disclaimer, the term of this patent is extended or adjusted under 35 U.S.C. 154(b) by 0 days.

(21) Appl. No.: 11/361,428

(22) Filed: Feb. 24, 2006

(51) Int. Cl.
*A01H 5/00* (2006.01)

(52) U.S. Cl. ..... Plt./197; Plt./198; Plt./194

(58) Field of Classification Search ..... Plt./197, Plt./194
See application file for complete search history.

*Primary Examiner*—Anne Marie Grunberg
*Assistant Examiner*—S. B. McCormick-Ewoldt
(74) *Attorney, Agent, or Firm*—Townsend and Townsend and Crew LLP

(57) ABSTRACT

A new and distinct variety of peach tree is characterized by producing a large fruit for commercial harvesting and shipment between September 16–30 in the San Joaquin Valley of Central California. The new variety is somewhat similar to the fruit of 'Prima Gattie' (U.S. Plant Pat. No. 10,085) peach tree, but is distinguishable in that it produces fruit 7–10 days after 'Prima Gattie' with good blush color, juice production and excellent flavor.

1 Drawing Sheet

Latin name of the genus and species: The peach cultivar of this invention is botanically identified as *Prunus persica.*

Variety denomination: The variety denomination is 'GP10'.

BACKGROUND OF THE INVENTION

Commercially acceptable fruit or peach trees are abundant throughout the growing season. However, those commercial varieties of acceptable fruit of early maturing or late maturing varieties of peach are generally marginally successful because of small size, poor coloration, undesirable flavor, or poor handling characteristics. Those peach varieties that are early or late maturing fruit, but which possess characteristics that are more typical of fruit ripening at the height of the growing season, are of commercial value. This new variety of peach is such a variety of peach tree.

ORIGIN AND ASEXUAL REPRODUCTION

The variety was discovered as a seedling in September 2001 in a nursery row of a nursery owned and operated by the inventor near Sanger in the San Joaquin Valley of Central California. The new variety was asexually reproduced, true to type, and retained all of the distinctive characteristics through asexual propagation generations. Asexual reproduction occurred by grafting on 'Nemaguard' rootstock (non-patented) in 2002 under the direction of the inventor near Reedley.

BRIEF SUMMARY OF THE INVENTION

The 'GP10' peach tree is characterized by producing a large, high-quality, semi-clingstone fruit that have very good external coloration and are mature for commercial harvesting and shipping around September 16–30 in a normal year in the San Joaquin Valley of Central California. The new peach variety is most similar to the seed parent 'Prima Gattie' (U.S. Plant Pat. No. 10,085) from which it is a seedling, and produces fruit 7–10 days later. The pollen parent of 'GP10' is unknown. The color of 'GP10' resembles the coloration of the parent 'Prima Gattie' with the red blush covering from 30–80% of the fruit surface. There is no pollination requirement for the claimed peach tree.

BRIEF DESCRIPTION OF THE DRAWINGS

FIG. 1 illustrates, clockwise from top left: the front and back of whole leaves, whole leaves on a twig from a twig end, top, bottom and side views of the fruit displaying the characteristic skin color and shape, fruit cut in half displaying the flesh, pit cavity and pit in place, and pit.

DETAILED DESCRIPTION OF THE INVENTION

Referring more specifically to the horticultural details of the new and distinct variety of peach tree, the following has been observed under the ecological conditions prevailing at the orchard of origin which is located near the city of Reedley, Calif. in the San Joaquin Valley of Central California. All major color code designations are by reference to the Dictionary of Color by Maerz and Paul, First Edition, 1930. Common colors are also occasionally employed.

Tree:
- *Age of tree described herein.*—Four years old.
- *Size.*—Medium, 14–15 feet high, 12–14 feet wide.
- *Vigor.*—Very good.
- *Chilling requirements.*—Normal for peach in San Joaquin Valley of Central California.
- *Shape.*—Upright and spreading.

Trunk:
- *Size.*—Medium — 24 inches in circumference, 10 inches above ground.
- *Surface.*—Rough.
- *Color code.*—Pl.6 F9 Cameo Br.
- *Lenticels.*—Many — medium size and oval shape. Size — 0.16 inch length.

Branches:
- *Size.*—Medium — circumference 10¾ inches, 41 inches above crotch. Angle of scaffold branches — approximately 57°.

*Surface.*—Slightly smooth.
*Color code.*—1 year or older — Pl.6 H8 — Slate V. Immature — Pl.21 L6 — Parrot green.
*Lenticels.*—Many. Size — 0.16 inch length.

Leaves:
*Size.*—Medium and alternate. Length — 6.06–6.86 inch. Width — 1.65–1.77 inch.
*Color code.*—Upward disposable surface — Pl.22 L7 Art green. Downward disposable surface — Pl.20 K6 Piquant green.
*Shape.*—Lanceolate.
*Margin.*—Crenate.
*Leaf vein.*—Color code Pl.19 L5 Cosse green. Thickness — 0.079 inch.
*Glandular characteristics.*—Reniform — one to 4 smaller.
*Petiole.*—Medium. Length — 0.43–0.59 inch. Thickness — 0.079–0.12 inch. Color code — Pl.19 L5 Cosse green.
*Stem glands.*—Reniform, just below leaf base, opposite 2–4 small.
*Stipules.*—One 0.079 inch. Color Code — Pl.8 L6 Mirador, Argentina+Art Brown.

Flowers:
*Flower buds.*—Borne opposite, shape conic. Length — 0.28–0.39 inch. Width — 0.28–0.31 inch. Color — Pl.4 K8 Meadow Sweet.
*Calyx.*—5 sepals — P1.7 L7 Maroon with slight pubescence.
*Date of bloom.*—By February 23rd — 50–70%.
*Duration of bloom.*—Varies from five to ten days depending on climatic factors, particularly temperature.
*Bloom quantity.*—Showy and abundant — Color Code Pl.4 I8 Colonial Rose Diameter — 1.77–1.97 inch.
*Petals.*—5 with ovate shape, non-overlapping. Width — 0.91–1.02 inch. Length — 0.79–0.87 inch.
*Claws.*—0.079–1.02 inch.
*Pedicel.*—Short — 0.12 inch. Color — green at twig end and near Maroon at calyx end.
*Pistol.*—1, length 0.67–71 inch.
*Stamens.*—30–34.
*Filaments.*—Length — 0.51–67 inch. Color Code Pl.4 F4 Raspberry glace'.
*Anthers.*—Small — Color Code Pl.4 J11 Cognac.
*Nectaries.*—Range from Marathon Pl.11 H12 to dull color.

Fruit:
*Size.*—Large — 4 fruit — 2 lb. 3 oz. — 8¾ oz. Avg. (248 grams).
*Date of maturity.*—September16–30th.
*Size.*—Diameter in axial plane — 2.76–2.95 inch. Transverse in Suture Plane — 2.64–3.03 inch. Transverse at Right Angle to Suture Plane — 2.72–2.95 inch.
*Form.*—Symmetrical or Asymmetrical — asymmetrical with raised shoulder on ventral side.
*Suture.*—Slightly shallow with deeper penetration at apex end — woolshirt color.
*Ventral surface.*—Slightly irregular with raised coloration on ventral surface.
*Surface.*—Lipped on one side.
*Stem cavity.*—Generally — small to medium size, shoulders often creased with a groove where the fruit was attached to the branch. Width — 0.79–0.87 inch. Depth — 0.55–0.67 inch. Length — 1.34–1.38 inch. Shape — Oval. Stem — short — 0.20 inch length. Thickness — 0.079–0.169 inches.
*Base.*—Flat — truncate.
*Apex.*—Rounded with slight raise to raised tip.
*Pistil point.*—Mostly apical.
*Skin.*—Average for peach and tenacious to flesh at commercial maturity.
*Skin flavor.*—Neutral.
*Tendency of crack.*—None observed.
*Color.*—Generally skin coloration is uneven — a combination of Red Blush color and yellow ground color with blush color ranging from 30%–35% to 75–80%, ground color would then range 20–25% — 65–80%.
*Blush color.*—From Pl.6 L8 — Dark Cardinal to Pl.4 Ill Carnelian Copper.
*Ground colors.*—Pl.10 L4 Light chrome Y.
*Flesh.*—Flesh Color — Pl.10 E6 Cornhusk — from skin toward pit cavity about 0.39–0.47 inch, red streaks to pit cavity Pl.4 I5.
*Color of surface of pit cavity.*—Pl.4 Ill Carnelian Cooper to Pl.10 E6 — Cornhusk.
*Color of pit cavity.*—Pl.6 L6 — Chianti, Antique ruby+.
*Juice production.*—Becomes very juicy after ripening.
*Aroma.*—Very mild.
*Flesh texture.*—Very firm and finely textured.
*Ripening.*—Evenly throughout.
*Eating quality.*—Good.

Stone:
*Free stone or clingstone.*—Semi-clingstone. The stone is attached tightly to the flesh in the pit cavity at maturity. However, as the fruit fully ripens and softens, the stone will come loose from the flesh. Therefore, the stone surface is fully covered with short fibers and some adhering flesh.
*Fibers.*—Many in numbers over the entire surface of the stone and short-medium in length.
*Size.*—Medium — Length — 1.61 inch. Width — 1.18 inch. Thickness — 0.79 inch.
*Form.*—Usually oval.
*Apex.*—Variable, partially acute.
*Color.*—(Dry) — Pl.7 L6 India Red, Arabian Red+and Red Robin–.
*Base.*—Truncated with base angle oblique.
*Sides.*—Unequal.
*Surface.*—Nearly corrugated (grooved) overall with the apical end more so, basal end less so.
*Ventral angle.*—Width very narrow at apical end 0.079 inch to 0.20 inch in the middle.
*Wings.*—Somewhat erratic with more prominence in the middle and on the dorsal side.
*Dorsal edge.*—Very shallow, somewhat discontinued groove, less apparent at apical end.
*Hilum.*—Large, with heavy collar — 0.28 inch.
*Tendency to split.*—None observed.
*Use.*—Fresh market.
*Keeping quality.*—Excellent.
*Shipping and handling qualities.*—Excellent.

What is claimed is:

1. A new and distinct variety of peach tree having characteristics described and illustrated herein.

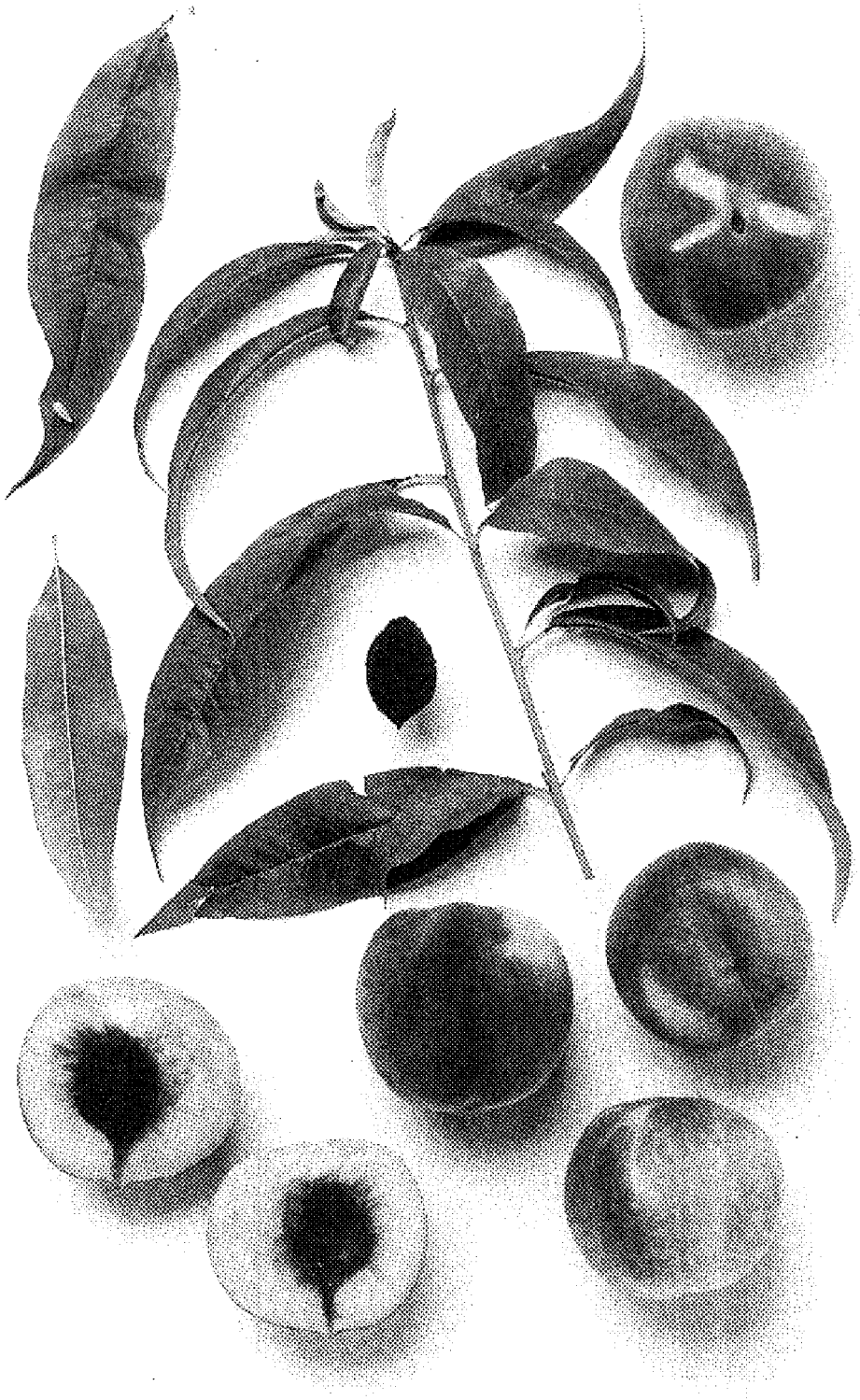

* * * * *